United States Patent [19]

Kobzina

[11] 4,287,213
[45] Sep. 1, 1981

[54] DICHLOROACYL DIPHENYL ETHER MITE OVACIDES

[75] Inventor: John W. Kobzina, Walnut Creek, Calif.

[73] Assignee: Chevron Research Company, San Francisco, Calif.

[21] Appl. No.: 126,254

[22] Filed: Mar. 3, 1980

[51] Int. Cl.³ .................... A01N 35/00; C07C 49/233
[52] U.S. Cl. .................................. 424/331; 568/331; 568/315; 568/316
[58] Field of Search ...................... 568/331, 315, 316; 424/331

[56] References Cited

U.S. PATENT DOCUMENTS

| | | | |
|---|---|---|---|
| 3,150,187 | 9/1964 | Cavallini et al. | 568/331 |
| 3,184,379 | 5/1965 | Lukes et al. | 568/316 |
| 3,941,830 | 3/1976 | Theissen | 560/21 |
| 3,966,826 | 6/1976 | Trosken | 71/121 |
| 4,031,131 | 6/1977 | Johnson | 560/21 |
| 4,093,446 | 6/1978 | Bayer et al. | 568/331 |
| 4,162,366 | 7/1979 | Engel | 568/331 |
| 4,164,408 | 8/1979 | Theissen | 71/98 |
| 4,164,409 | 8/1979 | Theissen | 71/98 |
| 4,164,410 | 8/1979 | Theissen | 71/98 |
| 4,209,532 | 6/1980 | Wheeler | 424/331 |

FOREIGN PATENT DOCUMENTS 1502538 4/1974 France.
50-125026 10/1975 Japan ..................... 568/331
51-58228 3/1976 Japan.

OTHER PUBLICATIONS

Org. Syn. Coll. vol. 3, p. 538 (1955).
Aston et al., Org. Syn. Col. vol. 3, pp. 538–541 (1955).
Wyman et al., J. Org. Chem., vol. 29, pp. 1956–1960 (1964).
Pacchiano et al., Chem. Abst., vol. 61, #3440f.
Cavallini et al., Chem. Abst., vol. 59, #8639h.

*Primary Examiner*—Natalie Trousof
*Assistant Examiner*—James H. Reamer
*Attorney, Agent, or Firm*—J. A. Buchanan, Jr.; T. G. DeJonghe; L. S. Squires

[57] ABSTRACT

Compounds having the formula

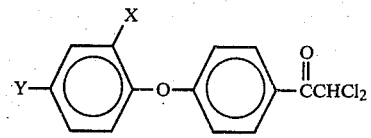

wherein one of X or Y is chloro and the other is trifluoromethyl or wherein X is hydrogen and Y is chloro and methods of preparing said compounds.

The compounds can be prepared by the reaction of the corresponding 1-acetyl substrate with chlorine or sulfuryl chloride and are useful as mite ovacides.

5 Claims, No Drawings

DICHLOROACYL DIPHENYL ETHER MITE OVACIDES

BACKGROUND OF THE INVENTION

1. Field of the Invention

This invention relates to 1-dichloroalkanoyl-substituted phenoxy benzenes and to methods for preparing such compounds. In a further aspect the invention relates to mite ovacide compositions comprising one or more of the above compounds. In another aspect the invention relates to methods of killing mite eggs by the applications of the aforementioned compounds and compositions.

2. Prior Art

It is well recognized that plant mites are one of the most destructive plant pests. Because of their small size these pests usually go unrecognized or undiscovered until the plants have been very significantly damaged either by the mites themselves or by the diseases they carry or render the plants susceptible to. Thus, by the time the mites are discovered, the plant may have to be destroyed or is often permanently stunted. Therefore, it would be very desirable to develop new miticides and mite ovacides which can be safely applied to vegetation.

Japanese Pat. No. 75-58,228 discloses that certain 1-acyl-4-(2-halo or nitro-4-trifluoromethylphenoxy)-benzene, including 1-acetyl-4-(2-chloro-4-trifluoromethylphenoxy) benzene, are good herbicides. U.S. Pat. No. 4,031,131 discloses the preparation of 1-formyl-4-(2-chloro-4-trifluoromethylphenoxy)benzene as herbicides and U.S. Pat. No. 3,966,826 discloses the preparation of 1-hydroxy-4-(2-chloro-4-trifluoromethylphenoxy)benzene, and salts thereof, as intermediates for the corresponding 1-oxypropionic acid herbicides.

The preparation of dichloroacetophenone via the chlorination of acetophenone in glacial acetic acid is disclosed in Organic Synthesis Collective Volume 3, p. 538 (1955).

U.S. Pat. Nos. 3,941,830; 4,164,408; 4,164,409; and 4,164,410 disclose certain 2-nitro-5-(substituted and unsubstituted phenoxy) benzoates and teach that such compounds exhibit herbicidal properties.

U.S. Pat. No. 3,941,830 also discloses that French Pat. No. 1,502,538 suggests using 4-phenoxybenzoic acids as herbicides.

SUMMARY OF THE INVENTION

The present invention provides novel compounds and compositions having substantial mite ovacide activity which can be applied to vegetation without injuring the vegetation. The compounds of the invention can be represented by the following generic formula:

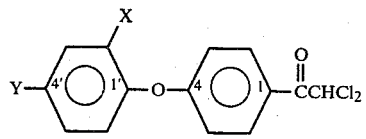

(I)

wherein one of X or Y is chloro and the other is trifluoromethyl or wherein X is hydrogen and Y is chloro.

In one embodiment the invention comprises a process for preparing the compounds of the invention which comprises contacting the corresponding 1-alkanoyl-4-(substituted phenoxy)benzene starting material with chlorine under reactive conditions.

In a further embodiment the invention comprises a process for preparing the present compounds which comprises contacting the corresponding 1-alkanoyl-4-(substituted phenoxy)benzene starting material with sulfuryl chloride under reactive conditions thereby yielding the corresponding dichloroalkanoyl compounds of the invention.

In still further embodiment the invention provides mite ovacide compositions comprising an effective amount of one or more of the compounds of the invention and a compatible carrier.

In still another embodiment the invention comprises a method of killing mite eggs which comprises applying an effective amount of the compounds and/or compositions of the invention to mite eggs or to vegetation and surfaces where mite eggs are likely to be laid.

The invention will be further described hereinbelow.

FURTHER DESCRIPTION OF THE INVENTION AND PREFERRED EMBODIMENTS

Considering the invention in greater detail, the compounds of the invention are:

1-dichloroacetyl-4-(2-chloro-4-trifluoromethylphenoxy)-benzene; 1-dichloroacetyl-4-(2-trifloromethyl-4-chlorophenoxy)-benzene; and 1-dichloroacetyl-4-(4-chlorophenoxy)-benzene.

I have found that these compounds unexpectantly exhibit mite ovacide activity and further exhibit only minimal herbicidal activity. Further, based on mite ovacide tests, best results are obtained using 1-dichloroacetyl-4-(2-chloro-4-trifluoromethylphenoxy)-benzene and 1-dichloroacetyl-4-(2-trifluoromethyl-4-chlorophenoxy)-benzene. The unexpectedness of this activity and the superiority of the aforementioned two compounds can readily be appreciated from Example 3 set forth hereinbelow on page 11.

The compounds of the present invention can be prepared by the following process which can be schematically represented by the following overall reaction equation:

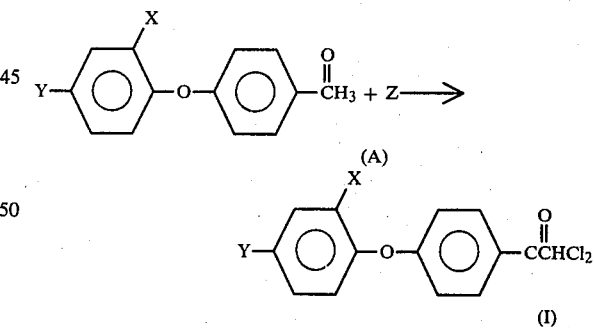

wherein Z is chlorine or sulfuryl chloride and X and Y are as defined hereinabove with respect to formula (I).

This process can be conveniently effected by contacting the appropriate starting material of formula (A), having the desired X and Y substituents with either chlorine or sulfuryl chloride. Preferably the process is conducted in an inert organic solvent and can be conveniently conducted by the simple expedient of bubbling chlorine into, or adding sulfuryl chloride to, a solution or mixture of the compound of formula (A) and the inert organic solvent. The process is typically conducted at temperatures in the range of about from 0° to 100° C. for about from 0.5 to 2 hours preferably from about from 0.5 to 1.5 hours. It is preferable to conduct the process at temperatures in the range of about from 50° to 70° C. to minimize the formation of trichloroacetyl analogs. Typically a mol ratio chlorine ($Cl_2$) or sulfuryl chloride ($SO_2Cl$) to compound of formula (A) the range of about from 2 to 3 mols and preferably about from 2 to 2.2 mols of chlorine or sulfuryl chloride per mol compound of formula (A) is used.

Best results are typically obtained by conducting the process at temperatures in the range of about from 55° to 65° C. for about 0.5 to 1 hour using a mol ratio compound of chlorine of sulfuryl chloride to compound of formula (A) in the range of about from 2 to 2.2 mols of chlorine or sulfuryl chloride per mol of compound formula (A).

Where chlorine is used, suitable inert organic solvents which can be used include, for example, glacial acetic acid, carbon tetrachloride, chloroform, and the like and compatible mixtures thereof and especially glacial acetic acid. Where sulfuryl chloride is used, suitable inert organic solvents which can be used, include, for example, carbon tetrachloride, chloroform, methylene chloride and the like and compatible mixtures thereof.

The product of formula (I) can be recovered by any suitable separation and purification procedures such as, for example, chromatography, recrystallization and trituration. Suitable separation and purification procedure are, for example, illustrated by the examples set forth hereinbelow, however, other procedures could also be used.

Generally the starting materials of formula (A) can be conveniently prepared by the reaction of the appropriate 1-alkanoyl-4-fluorobenzene with a disubstituted sodium phenoxide having the appropriate X and Y substituents or by the reaction of the sodium salt of 4-hydroxyacetophenone with an appropriately substituted di- or tri-substituted benzene containing a displacable halogen.

The starting materials of formula A can also be prepared via a Friedel-Crafts reaction by reacting the appropriate 4-(substituted-phenoxy)-benzene compound having the desired X and Y substituents with acetic anhydride or acetyl chloride in the presence of a suitable Friedel-Crafts catalyst (e.g., $FeCl_3$, $AlCl_3$, etc.). In the case where the phenoxybenzene substrate has a trifluoromethyl substituent, Friedel-Crafts catalysts, such as aluminum chloride, which rapidly attack trifluoromethyl groups, should, of course, not be used.

A preferred process for preparing large quantities of the compounds of my invention which eliminates the need for sophisticated purification procedures is described by F. J. Freenor in U.S. Ser. No. 126,252 filed on even date herewith, hereby incorporated by reference, and illustrated by Examples 5-7, set forth hereinbelow.

It should also be appreciated that where typical and preferred reaction conditions have been given herein that the described processes may also be conducted at conditions outside of these ranges though generally with poor results or economies.

UTILITY

The compounds of the invention exhibit substantial mite ovacide activity and thus are useful for killing mite eggs. The compounds can be applied, in an effective mite ovacidal amount, to mite eggs, or surfaces subject to mite eggs, via any suitable procedures. Importantly, the present compounds do not exhibit any significant herbicidal activity and thus can be safely applied to vegetation to control mites via the destruction of their eggs.

The present compounds can be stored and applied as formulations incorporated with compatible biologically inert extenders or carriers such as are typically employed for facilitating dispersion of active ingredients for agricultural chemical applications. These formulations typically contain about from 0.5 to 95 wt % of the present compound, and optionally can contain compatible miticides, insecticides, chemical applications. These formulations typically contain about from 0.5 to 95 wt% of the present compound, and optionally can contain compatible miticides, insecticides, fungicides, etc., and the remainder biologically inert material including dispersing agents, emulsifying agents, wetting agents and carriers.

Such formulation can be formulated as sprays, dusts, or granules and applied to mite eggs and/or their environment or hosts susceptible to mite attack. They can be formulated as granules of large particle size, as powdery dusts, as wettable powders, as emulsifiable concentrates, as solutions, or as any of several other known types of formulations, depending on the desired mode of application. (Wettable powders generally refers to a form of finely divided particles which disperse readily in water or other dispersant.) Typical carriers include fuller's earth, kaolin clays, silicas, and other highly absorbent, readily wet, inorganic diluents. Typical wetting, dispersing, or emulsifying agents used in agricultural formulations include, for example, the alkyl and alkylaryl sulfonates and sulfonates and their sodium salts; alkylamide sulfonates, including fatty methane taurides, alkylaryl polyether alcohols, sulfated higher alcohols, and polyvinyl alcohols; polyethylene oxides; sulfonated animal and vegetable oils; sulfonated petroleum oils; fatty acid esters of polyhydric alcohols and the ethylene oxide addition products of such esters; and the addition products of long chain mercaptans and ethylene oxide. Many other types of useful surface active agents are available in commerce. The surface active agent, when used, normally comprises from one percent to fifteen percent by weight of the pesticidal composition.

Dusts are freely flowing admixtures of the active ingredient with finely divided solids such as talc, natural clays, kieselguhr, pyrophyllite, chalk, diatomaceous earths, calcium phosphates, calcium and magnesium carbonates, sulfur, lime, flours, and other organic and inorganic solids which act as dispersants and carriers for the toxicant. These finely divided solids have an average particle size of less than about fifty microns. A typical dust formulation useful herein contains about 65–80 wt % silica and 35–20 wt % of the compound(s) of the invention.

Useful liquid concentrates include the emulsifiable concentrates, which are homogeneous liquid or paste compositions which are readily dispersed in water to other dispersant, and can consist entirely of the compound(s) of the invention with a liquid or solid emulsifying agent, or can also contain a liquid carrier, such as xylene, heavy aromatic naphthas, isophorone, and other non-volatile organic solvents. These concentrates are usually dispersed in water, or other liquid carrier, and then applied as a spray or paint to the area to be treated.

Optimum formulation concentrations and the manner and frequency of application may vary somewhat with the particular species of mite eggs, the degree of infestations, the environment (e.g. rainfall), and can be obtained by routine experimentation.

A further understanding of the invention can be had from the following non-limiting examples. Wherein, unless expressly stated to the contrary, all temperatures and temperature ranges refer to the centigrade (or Celsius) system and the term "ambient", "room temperature" refer to about 20°–25° C. The term "percent" or "%" refers to weight percent and the term "mol" or "mols" refers to gram mols. The term "equivalent" refers to the quantity of the reagent equal in mols to the mols of the preceding or succeeding reactants recited in that example in terms of finite mols or a finite weight or volume. Also, unless expressly stated to the contrary, where the compounds exist as optical isomers, racemic mixtures are used as a starting material and correspondingly racemix mixtures are obtained as products. Where given proton magnetic resonance spectrum (n.m.r.) are determined at 60 mHz. and signals are assigned as singlet (s), broad singlet (bs), doublets (d), double doublets (dd), triplets (t), double triplets (dt), quartets (q) and multiplets (m).

PREPARATION A

This preparation illustrates the preparation of the starting materials of formula (A).

1-Acetyl-(2-Chloro-4-Trifluoromethylphenoxy)-Benzene

In this preparation 25.3 g of 4-hydroxyacetophenone, 51.4 g of potassium carbonate, and 40 g of 3,4-dichlorobenzotrifluoride were mixed with 250 ml of dimethylformamide. The resulting solution was heated 3 hours at 80° C.; 5 hours at 110° C. and 16 hours at reflux. The dimethylformamide was then removed by evaporation and 300 ml of water and 400 ml of chloroform were added to the remaining material. The organic layer was separated, washed with 10% aqueous sodium hydroxide, then twice with water, dried over magnesium sulfate, and evaporated to dryness affording an oil. The oil was then chromatographed on a silica gel column eluting with 10% (vol.) tetrahydrofuranhexane. The product eluted as 11.26 g of a clear brown oil. The infrared spectrum and nmr spectrum of this product conformed to the proposed structure 1-acetyl-4-(2-chloro-4-trifluorophenoxy)-benzene.

Similarly, by following the same procedure but respectively replacing 3,4-dichlorobenzotrifluoride with 2,5-dichlorobenzotrifluoride and 1,4-dichlorobenzene the compounds 1-acetyl-(2-trifluoromethyl-4-chlorophenoxy)-benzene and 1-acetyl-(4-chlorophenoxy)-benzene are respectively prepared.

Preparation B

This preparation illustrates another procedure for preparing the starting materials of formula A.

1-Acetyl-4-(2-trifluoromethyl-4-chlorophenoxy)-Benzene

In this preparation 28.7 g of sodium hydroxide is dissolved in 500 ml of methanol. 50 g of 2-trifluoromethyl-4-chlorophenol is then added and the resulting solution then evaporated to dryness. 500 ml of toluene is added to the residue and the resulting solution again evaporated to dryness and the residue added to 650 ml of dimethylformamide. 49.5 g of 4-fluoroacetophenone is then added and the resulting solution refluxed for 45 hours. The solution is then filtered and the resulting filtrate evaporated to dryness. The residue is chromatographed on a silica gel column eluting with 5% (vol.) tetrahydrofuran-hexane. The product fractions are evaporated and the residue is then recrystallized from hexane affording 1-acetyl-4-(2-trifluoromethyl-4-chlorophenoxy)-benzene.

Similarly, by following the same procedure but respectively replacing 2-trifluoromethyl-4-chlorophenol with 2-chloro-4-trifluoromethylphenyl; and 4-chlorophenol, the following compounds are respectively prepared:

1-Acetyl-4-(2-chloro-4-trifluoromethylphenoxy)-benzene; and

1-Acetyl-4-(4-chlorophenoxy)-benzene.

Preparation C

The preparation illustrates the preparation of the starting materials of formula A via a Friedel-Crafts type reaction.

In this preparation 23.18 g (0.085 mol) of 4-(2-trifluoromethyl-4-chlorophenoxy)-benzene and 6.66 g (0.085 mol) of acetyl chloride are admixed with 200 ml of carbon disulfide and then 27.52 g (0.17 mol) of ferric chloride is added and the resulting mixture stirred at room temperature for about 23 hours. The mixture is then washed three times with ice-water, dried over magnesium sulfite and filtered. The filtrate is evaporated to dryness and the residue chromatographed on a silica gel column eluting with hexane; 5 vol.% tetrahydrofuran-hexane; and then 10 vol.% tetrahydrofuran-hexane, affording 1-acetyl-4-(2-trifluoromethyl-4-chlorophenoxy)-benzene.

Similarly, by following the same procedure but respectively replacing 4-(2-trifluoromethyl-4-chlorophenoxy)benzene with 4-(2-chloro-4-trifluoromethylphenoxy)-benzene and 4-(4-chlorophenoxy)-benzene the following compounds are respectively prepared:

1-acetyl-4-(2-chloro-trifluoromethylphenoxy)-benzene; and 1-acetyl-4-(4-chlorophenoxy)-benzene.

EXAMPLE 1

This example illustrates the method of the invention, for preparing the compounds of the invention, using chlorine.

In this example 6 grams of 1-acetyl-4-(2-chloro-4-trifluoromethylphenoxy)-benzene was added to 200 ml of glacial acetic acid and the mixture heated to 60° C. The resulting solution was maintained at this temperature and gaseous chlorine bubbled into the solution for 1 hour. The resulting mixture was then evaporated under vacuum affording a yellow oil. A small sample of the oil was examined by thin layer chromatography eluting with 5% by vol ethylene acetate/hexane and showed only a single spot. The yellow oil was then purified by liquid chromatography through a silica gel column again using a 5% by vol ethyl acetane/hexane solvent. The solvent was then removed by vacuum evaporation affording 5.6 grams of colorless oil which upon crystallization afforded 1-dichloroacetyl-4-(2-chloro-4-trifluoromethylphenoxy)-benzene as a white solid having a melting point of 41°–42° C.

Similarly by following the same procedure but respectively using 1-acetyl-4-(2-trifluoromethyl-4-chlorophenoxy)-benzene and 1-acetyl-4-(4-chlorophenoxy)-benzene in place of 1-acetyl-4-(2-chloro-4-trifluoromethylphenoxy)-benzene the following compounds are respectively prepared:

1-dichloroacetyl-4-(2-trifluoromethyl-4-chlorophenoxy)-benzene (oil) and 1-dichloroacetyl-4-(4-chlorophenoxy)-benzene (yellow oil).

EXAMPLE 2

This example illustrates the method of the invention, for preparing the compounds of the invention, using sulfuryl chloride.

In this example 11.26 g of 1-acetyl-4-(2-chloro-4-trifluoromethylphenoxy)-benzene was dissolved in 200 ml of carbon tetrachloride. To this solution, 4.8 g of sulfuryl chloride, dissolved in 20 ml of carbon tetrachloride, was added dropwise. The resulting solution was stirred overnight (about 12 hours) at room temperature and then refluxed for 0.5 hours. An additional 1 g of sulfuryl chloride was then added and the mixture stirred for another hour at room temperature. The mixture was then evaporated yielding an oil which upon high pressure liquid chromatography, eluting with 5% vol. tetrahydrofuran-hexane, afforded 2.7 g of 1-dichloroacetyl-(2-chloro-4-trichloromethylphenoxy)-benzene (yellow oil) as the first material eluted.

Similarly, by following the same procedure but respectively using 1-acetyl-4-(2-trifluoromethyl-4-chlorophenoxy)-benzene and 1-acetyl-4-(4-chlorophenoxy)-benzene in place of 1-acetyl-4-(2-chloro-4-trifluoromethylphenoxy) benzene, the following compounds are respectively prepared:

1-dichloroacetyl-4-(2-trifluoromethyl-4-chlorophenoxy)-benzene (oil); and 1-dichloroacetyl-4-(4-chlorophenoxy)-benzene (yellow oil).

EXAMPLE 3

In this example the compounds of the invention were tested for mite ovacide activity along with a number of closely related compounds, which I have discovered, to illustrate the mite ovacide activity of the compounds of the invention and also to illustrate the uniqueness of this property.

In this example, lima bean leaves are infested with two-spotted spider mites (*Tetranychus urticae Koch*) the mites were allowed to lay eggs on the leaves. The eggs are visually counted and the test conducted using 20 eggs per replica. After 48 hours, the leaves were dipped into a water/acetone solution containing a small amount of a nonionic surfactant and 40 ppm of the compound to be tested. The treated leaves were then maintained at 85° F. Seven days after treatment the leaves were examined and egg mortality (non-hatching eggs) was determined. (After the 7 day holding period, any adults remaining will have died and all eggs which are capable of hatching will have hatched. Hatched eggs can be detected by their clear, spherical shells and they usually reflect the light when viewed under a microscope. Dead eggs appear more solid since they usually contain a desiccated embryo or yolk.) Percent egg mortality was calculated for each replica test on the basis of 100 X non-hatching eggs divided by a total number of eggs in the replica and the percent egg mortality given as the average value of all the replicas tested for a given compound.

The results of these tests are summarized in the following table, wherein compound identification numbers are identified hereinbelow in Tables A and B. The compounds of the invention are compound ID Nos. 1, 2 and 3 and are identified in Table A. The remaining compounds are structurally similar compounds and are identified in Table B.

TABLE 1

| Mite Ovacide Activity | |
|---|---|
| Compound ID No. | Percent Egg Mortality |
| Control* | 0 |
| 1 | 96 |
| 2 | 85 |
| 3 | 22 |
| 4 | 0 |
| 5 | 0 |
| 6 | 0 |
| 7 | 0 |
| 8 | 0 |

*Untreated Mite Eggs

TABLE A

| ID No. | Compound |
|---|---|
| 1 | 1-dichloroacetyl-4-(2-chloro-4-trifluoromethylphenoxy)-benzene; |
| 2 | 1-dichloroacetyl-4-(4-chloro-2-trifluoromethylphenoxy)-benzene |
| 3 | 1-dichloroacetyl-4-(4-chlorophenoxy)-benzene. |

TABLE B

| ID No. | Compound |
|---|---|
| 4 | 1-dichloroacetyl-4-(2,4-dichlorophenoxy)-benzene |
| 5 | 1-dichloroacetyl-4-(4-trifluoromethylphenoxy)-benzene |
| 6 | 1-chloroacetyl-4-(2-chloro-4-trifluoromethylphenoxy)-benzene |
| 7 | 1-trichloroacetyl-4-(2-chloro-4-trifluoromethylphenoxy)-benzene |
| 8 | 1-(2,2-dichloropropionyl)-4-(2-chloro-4-trifluoromethylphenoxy)-benzene. |

The comparison compounds listed in Table B were prepared by the same general procedures as described above with respect to the present invention but using the appropriate starting materials.

As can be seen from the results set forth in the above Table I the compounds of the invention exhibited mite ovacide activity, whereas the structurally related compounds failed to show any mite ovacide activity. Further as between the compounds of the invention both 1-dichloroacetyl-4-(2-chloro-4-trifluoromethylphenoxy)-benzene and 4-(4-chloro-1-trifluoromethylphenoxy)-benzene showed exceptional mite ovacide activity and especially so the former compound.

EXAMPLE 4

In this example, the compounds of the invention were examined for both pre-emergence and post-emergence herbicidal activity.

PRE-EMERGENT HERBICIDE TEST

The pre-emergence herbicidal activity was determined in the following manner.

An acetone solution of the test compound was prepared by mixing 750 mg compound, 220 mg of a nonionic surfactant and 25 ml of acetone. This solution was added to approximately 125 ml of water containing 156 mg of surfactant.

Seeds of the test vegetation were planted in a pot of soil and the test compound solution was sprayed uniformly onto the soil surface at a dose of 27.5 micrograms/mc$^2$. The pot was watered and placed in a greenhouse. The pot was watered intermittently and was observed for seedling emergency, health of emerging seedlings, etc., for a 3-week period. At the end of this period, the herbicidal effectiveness of the imidazolidine-dione was rated based on the physiological observations. A 0-to-100 scale was used, 0 representing no phytotoxicity and 100 representing complete kill. The result of these tests are summarized in Table 2, hereinbelow.

POST-EMERGENT TEST

The test compound was formulated in the same manner as described above for the pre-emergent test. The concentration of the test compound in this formulation was 5000 ppm. This formulation was uniformly sprayed on 2 similar pots of 24-day-old plants (approximately 15 to 25 plants per pot) at a dose of 27.5 micrograms/cm$^2$. After the plants had dried, they were placed in a greenhouse and then watered intermittently at their base, as needed. The plants were observed periodically for phytotoxic effects and physiological and morphological responses to the treatment. After 3 weeks, the herbicidal effectiveness of the compound was rated based on these observations. A 0to-100 scale was used, 0 representing no phytotoxicity and 100 representing complete kill. The results of these tests are summarized in Table 3.

The compounds tested are identified hereinabove in Table A of Example 3 and the results of these tests are summarized in Table 2 with respect to pre-emergent herbicidal activity and Table 3 with respect to post-emergent herbicidal activity.

collected 4910 ml of which 690 ml were water). The temperature of the remaining reaction mixture, now containing sodium phenolate, was permitted to drop to 155° C. and 44 g of powdered copper was added. 4730 g (22 mol) of 1,2-dichloro-4-trifluoromethylbenzene was then added dropwise while maintaining the reaction mixture at 153°–155° C. After addition of the 1,2-dichloro-4-trifluoromethylbenzene, the reaction mixture was maintained at 155° C. for about 30 minutes and then allowed to stand overnight (about 12 hours) at room temperature. The reaction mixture was poured onto cold 0.5% HCl. phase separated and extracted with methylene chloride. Combined organics were washed with 5% sodium hydroxide and with water, dried over magnesium sulfate and silica, and filtered. The filtrate was then stripped (evaporated) affording 5906 g of 4-(2-chloro-4-trifluoromethylphenoxy)benzene as a yellow oil.

Similarly, 4-(2-trifluoromethyl-4-chlorophenoxy)-benzene is prepared by following the same procedure but using 1,4-dichloro-2-trifluoromethylbenzene in place of 1,2-dichloro-4-trifluoromethylbenzene.

EXAMPLE 6

This example illustrates the preparation of 1-acetyl-4-(substituted phenoxy)benzenes.

In this example 1079 g (13.75 mols) of acetyl chloride was slowly added over one hour to a stirred mixture containing 2230 g (13.75 mols) of ferric chloride in 3450 ml of methylene chloride maintained at 16½ to 17° C.

TABLE 2

| Compound ID No. | Concentration Micrograms Per Cm$^2$ | Pre-Emergence Herbicidal Activity | | | | | | | |
|---|---|---|---|---|---|---|---|---|---|
| | | Broad-Leaf Plants % kill | | | Grasses % kill | | | Crops % kill | |
| | | Mustard | Pigweed | Lambsquarters | W. Oats | Watergrass | Crabgrass | Soybean | Rice |
| 1 | 27.5 | 0 | 0 | 0 | 0 | 0 | 0 | 0 | 0 |
| 2 | 27.5 | 0 | 0 | 0 | 0 | 0 | 0 | 0 | 0 |
| 3 | 27.5 | 0 | 0 | 0 | 0 | 0 | 0 | 0 | 0 |

TABLE 3

| Compound ID No. | Concentration Micrograms Per Cm$^2$ | Post-Emergence Herbicidal Activity | | | | | | | |
|---|---|---|---|---|---|---|---|---|---|
| | | Broad-Leaf Plants % kill | | | Grasses % kill | | | Crops % kill | |
| | | Mustard | Pigweed | Lambsquarters | W. Oats | Watergrass | Crabgrass | Soybean | Rice |
| 1 | 27.5 | 0 | 0 | 0 | 0 | 0 | 0 | 0 | 0 |
| 2 | 27.5 | 0 | 0 | 0 | 0 | 0 | 0 | 0 | 0 |
| 3 | 27.5 | 0 | 0 | 0 | 0 | 0 | 0 | 0 | 0 |

As can be seen from the above table the present compounds, although exhibiting substantial mite ovacide activity, exhibit virtually no herbicide activity and thus are especially useful as mite ovacides for plants.

EXAMPLE 5

Examples 5–7 illustrate the improved process described by F. J. Freenor in the aforementioned U.S. Patent application U.S. Ser. No. 126,252 for preparing relatively large quantities of the compounds of my invention.

In this example 2143 g (22.77 mol) of phenol and 906 g (22.66 mol) of sodium hydroxide were mixed together in a stirred mixture of 5.5 liters of dimethyl sulfoxide and 5.5 liters of toluene at room temperature. The mixture was then heated at reflux for 54 hours. The water formed by the reaction was removed from the reflux trap along with a substantial portion of the toluene and a small amount of the dimethyl sulfoxide (total volume 3408 g (12.5 mols) of (2-chloro-4-trifluoromethylphenoxy)benzene was then slowly added dropwise to the mixture over a period of 3 hours and 13 minutes, during which addition the temperature of the mixture was maintained between 18.5° to 20° C. (The rate of addition was controlled such that the (2-chloro-4-trifluoro-methylphenoxy)benzene was essentially consumed as it was added.) The reaction although essentially complete was stirred overnight at room temperature (about 20°). A sample was then examined by gas chromatography and indicated less than 2% of the (2-chloro-4-trifluoromethyl-phenoxy)benzene starting material remained in the reaction mixture.

The reaction mixture was then cooled to 15° C. and 6250 ml of water was slowly added over 1½ hours while maintaining the temperature of the reaction mixture at 17°–19° C. The resulting mixture was then stirred for 1 hour at room temperature and then 6250 ml of hexane was added. The mixture was phase-separated and extracted with hexane. The combined organics were washed with water and with 5% sodium bicarbonate, dried over magnesium sulfate and silica, filtered and stripped. The resulting oil/solid was recrystallized from isopropyl alcohol-hexane, yielding 2073 g of 1-acetyl-4-(2-chloro-4-trifluoromethylphenoxy)benzene.

The mother liquor was purified through formation of the semi-carbazone by adding the stripped mother liquor (913 g) to a solution of equimolar amounts of semicarbazide hydrochloride (about 2.92 mol) and sodium acetate in water-ethanol. The mixture was heated at 32°-76° for 3-4 hours. The resultant white solid was freed of impurities by rinsing with ethanol and hexane.

This solid was refluxed for 1 hour in a mixture of 350 ml concentrated hydrochloric acid, 1 liter water, and 500 ml ethanol. The mixture was cooled, phase-separated and extracted with hexane. The combined organics were washed with water and with 5% aqueous NaOH, dried over magnesium sulfate, filtered, stripped and recrystallized from isopropyl alcoholhexane yielding 330 g of 1-acetyl-4-(2-chloro-4-trifluoromethylphenoxy)benzene.

Similarly, 1-acetyl-(2-trifluoromethyl-4-chlorophenoxy)benzene is prepared by following the same procedure but using (2-trifluoromethyl-4-chlorophenoxy)benzene in place of (2-chloro-4-trifluoromethylphenoxy)benzene.

EXAMPLE 7

This example illustrates the preparation of 1-dichloroacyl-4-(substituted phenoxy)benzenes.

In this example 4532 g (14.4 m) of 1-acetyl-4-(2-chloro-4-trifluoromethylphenoxy)benzene was admixed with 4550 ml of glacial acetic acid. The temperature of the mixture was raised to 38° C. and chlorine was then bubbled into the mixture for 2½ hours. During this period the temperature of the mixture rose to a high of 45° C. The addition of chlorine was then discontinued overnight (reaction mixture allowed to stand at room temperature) and was continued the following morning for another 7½ hours. Upon resumption of the addition of chlorine the reaction mixture was at 15° C. and rose to a high of 56° C. during the addition of chlorine. The majority of the chlorine was added while maintaining a reaction mixture temperature at 45°-55° C. It was noted that when a total 2231 g of chlorine had been taken up the exotherm stopped. Another 18 g of chlorine was bubbled into the reaction mixture (total chlorine added was 2349 g) and the mixture allowed to stand at room temperature for 48 hours.

The reaction mixture was poured onto ice-water, and extracted with methylene chloride. The combined organics were washed with water and with sodium bicarbonate solution, dried over magnesium sulfate and silica, filtered and stripped to an orange oil. Crystallization from isopropyl alcohol-hexane yielded 4371 g. 1-dichloroacetyl-4-(2-chloro-4-trifluoromethylphenoxy)benzene [white solid: m.p. 40°-41° C.].

Thus, it can be seen that the above processes of the invention afford a very pure product without resorting to sophisticated purification procedures.

Similarly, 1-dichloroacetyl-4-(2-trifluoromethyl-4-chlorophenoxy)benzene is prepared by using 1-acetyl-4-(2-trifluoromethyl-4-chlorophenoxy)benzene.

Obviously many modifications and variations of the invention, described hereinabove and below in the claims, can be made without departing from the essence and scope thereof.

What is claimed is:

1. A compound having the formula

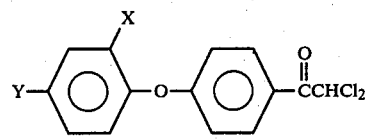

wherein one of X or Y is chloro and the other is trifluoromethyl.

2. The compound of claim 1 wherein said compound is 1-dichloroacetyl-4-(2-chloro-4-trifluoromethylphenoxy)-benzene.

3. The compound of claim 1 wherein said compound is 1-dichloroacetyl-4-(2-trifluoromethyl-4-chlorophenoxy)-benzene.

4. A mite ovacide composition which comprises an effective amount of the compound of claim 1 and an inert carrier.

5. A method of killing mite eggs which comprises applying a mite ovacide effective amount of the compound of claim 1 to said mite eggs of their habitat.

* * * * *